US012770261B2

(12) United States Patent
Shah

(10) Patent No.: US 12,770,261 B2
(45) Date of Patent: Oct. 20, 2026

(54) SYSTEMS AND METHODS FOR RECOGNIZING CHILDREN SUFFERING COWS' MILK ALLERGY

(71) Applicant: Mead Johnson Nutrition Company, Evansville, IN (US)

(72) Inventor: Neil Shah, London (GB)

(73) Assignee: Mead Johnson Nutrition Company, Evansville, IN (US)

( * ) Notice: Subject to any disclaimer, the term of this patent is extended or adjusted under 35 U.S.C. 154(b) by 477 days.

(21) Appl. No.: 18/251,980

(22) PCT Filed: Nov. 10, 2021

(86) PCT No.: PCT/EP2021/081265
§ 371 (c)(1),
(2) Date: May 5, 2023

(87) PCT Pub. No.: WO2022/101280
PCT Pub. Date: May 19, 2022

(65) Prior Publication Data

US 2024/0013396 A1 Jan. 11, 2024

(30) Foreign Application Priority Data

Nov. 10, 2020 (GB) .................................... 2017750
Jun. 10, 2021 (EP) .................................... 21178884

(51) Int. Cl.
*G06T 7/00* (2017.01)
*A61B 5/00* (2006.01)
(Continued)

(52) U.S. Cl.
CPC .......... *G06T 7/0014* (2013.01); *A61B 5/1114* (2013.01); *A61B 5/1128* (2013.01);
(Continued)

(58) Field of Classification Search
CPC .................. G06T 7/0014; G06T 7/248; G06T 2207/10016; G06T 2207/30196;
(Continued)

(56) References Cited

U.S. PATENT DOCUMENTS

2007/0016109 A1* 1/2007 Orito .................... A61B 5/1124 600/595
2009/0062696 A1* 3/2009 Nathan ................ A61B 5/1101 600/595

(Continued)

OTHER PUBLICATIONS

Nalbantoglu et al, ("Sandifer's Syndrome: a Misdiagnosed and Mysterious Disorder," Iranian Journal of Pediatrics, vol. 23, No. 6, Jan. 25, 2013 pp. 715-716) (Year: 2013).*

(Continued)

*Primary Examiner* — Amara Abdi
(74) *Attorney, Agent, or Firm* — DUNLAP CODDING, P.C.

(57) ABSTRACT

A system for use in recognising an infant suffering from cow's milk allergy is described which comprises measuring body movement of the infant, wherein the system comprises computer processing means configured, in use, to: receive a video including a sequence of images of an infant moving; detect the infant in the video images; locate at least one reference point on the infant; measure a vector of movement for the or each reference point over a sequence of said images; compare the or each vector of movement against a directory of corresponding vectors of movement and determine a proximity value; generate a communication in which the proximity value is used to provide an indication of whether the infant is suffering from cow's milk allergy. Methods for recognising cow's milk allergy in an infant, computer-implemented methods for use in recognising an infant suffering from cow's milk allergy and non-transitory processor-readable mediums having instructions stored (Continued)

thereon, which when executed by one or more processors, cause the processors to implement said methods are also described.

14 Claims, 2 Drawing Sheets

(51) Int. Cl.
*A61B 5/11* (2006.01)
*G06T 7/246* (2017.01)
*G16H 30/40* (2018.01)
*G16H 50/20* (2018.01)

(52) U.S. Cl.
CPC .............. *A61B 5/411* (2013.01); *G06T 7/248* (2017.01); *G16H 30/40* (2018.01); *G16H 50/20* (2018.01); *A61B 2503/04* (2013.01); *G06T 2207/10016* (2013.01); *G06T 2207/30196* (2013.01)

(58) Field of Classification Search
CPC ..... A61B 5/1114; A61B 5/1128; A61B 5/411; A61B 2503/04; A61B 5/1121; A61B 5/1122; A61B 5/0022; A61B 5/7267; G16H 30/40; G16H 50/20; G06V 40/20; G06V 20/52
See application file for complete search history.

(56) References Cited

U.S. PATENT DOCUMENTS

| | | | | |
|---|---|---|---|---|
| 2015/0288877 | A1 | 10/2015 | Glazer | |
| 2021/0293634 | A1* | 9/2021 | Ghose .................. | A61B 5/7246 |

OTHER PUBLICATIONS

Bamji et al., ("Treatment of Sandifer Syndrome with an Amino-Acid-Based Formula," American Journal of Perinatology Reports, vol. 5, No. 1, Mar. 4, 2015 pp. 51-52) (Year: 2015).*

Miller et al., "Prognostic Significance of Subgroup Classification for Infant Patients with Crying Disorders: a Prospective Cohort Study," The Journal of the Canadian Chiropractic Association, vol. 56, No. 1, Mar. 1, 2021, pp. 40-48 (Year: 2021).*

International Search Report and Written Opinion from Application No. PCT/EP2021/081265 dated Feb. 10, 2022.

Nalbantoglu, et al., "Sandifer's Syndrome: a Misdiagnosed and Mysterious Disorder," Iranian Journal of Pediatrics vol. 23, No. 6, Jan. 25, 2013 pp. 715-716.

Bamji, et al., "Treatment of Sandifer Syndrome with an Amino-Acid-Based Formula," American Journal of Perinatology Reports, vol. 5, No. 1, Mar. 4, 2015 pp e51-e52.

Miller, et al., "Prognostic Significance of Subgroup Classification for Infant Patients with Crying Disorders: a Prospective Cohort Study," The Journal of the Canadian Chiropractic Association, vol. 56, No. 1, Mar. 1, 2021 op 40-48.

* cited by examiner

SYSTEMS AND METHODS FOR RECOGNIZING CHILDREN SUFFERING COWS' MILK ALLERGY

FIELD OF THE INVENTION

The present invention is concerned with systems and methods that are configured to analyse a video image of an infant and recognise whether the infant is suffering from cow's milk allergy. The present invention is further concerned with systems and methods that are configured to analyse a video image of an infant to distinguish between an infant suffering from cow's milk allergy and an infant suffering with colic.

BACKGROUND

What is Colic?

Colic is not a disease nor a diagnosis, rather it is a catch-all term for excessive crying in seemingly healthy human infants where the resolution to said crying is the passage of time. The symptoms of colic can typically include crying for periods of three consecutive hours or more for three days within a period of a week. Other symptoms typically found with infants suffering with colic include: a clenching of their fists; going red in their face; bringing their knees toward their stomach or arching their backs; stomach upset or excessive flatulence; and/or being hard to soothe and settle. Colic is common in babies, approximately one in five infants will suffer from colic at some point in the first six months of their life. Clearly colic is unpleasant for both the infant and parents/carers of the suffering infant.

What is Cows' Milk Allergy?

Cows' milk allergy (CMA), also referred to as cows' milk protein allergy is one of the most common childhood food allergies, it is estimated to affect around 7% of human infants. CMA typically develops when cows' milk is first introduced into an infant's diet either via infant formula or when the infant starts eating solid foods. More rarely, CMA can affect infants who are exclusively breastfed because of cows' milk from the mother's diet passing to the infant through breast milk.

CMA is a reproducible immune-mediated allergic response to one or more proteins in cow's milk. It can be classified according to the underlying immune mechanism: Immunoglobulin (Ig)E-mediated food allergy produces immediate symptoms (Immediate CMA), which may affect multiple organ systems, typically up to 2 hours after cow's milk ingestion; non-IgE-mediated food allergy reactions usually manifest between 2 and 72 hours after cow's milk ingestion (Delayed CMA); and Mixed IgE and non-IgE allergic reactions are typically delayed.

CMA can cause a wide range of symptoms including: skin reactions (e.g. red itchy rashes or swelling of the lips/face/around eyes); digestive problems (e.g. stomach ache, vomiting, colic, diarrhoea, constipation); hay-fever-like symptoms (e.g. runny or blocked nose); eczema that is non-responsive to treatment. Occasionally CMA can cause severe allergic symptoms that present shortly after the infant is exposed to cows' milk such as swelling in the mouth or throat, wheezing, cough, shortness of breath.

Making an assessment of an infant with suspected cow's milk allergy requires the assessment of various facets of the infant and their symptoms. For non-IgE mediated allergy there is no diagnostic test. As such, the assessment relies on reviewing the infant's clinical history at a time when symptoms are difficult to segregate from normal very young infant symptoms. Such as assessment also requires questioning parents who can be exhausted and/or distressed which impacts the accuracy of their reporting. The assessment is further burdened with the clinician having a multitude of often complex guidelines to interpret. The assessment should further include the skin prick testing and/or serum-specific IgE allergy testing of the infant if there is suspected IgE-mediated allergy. The "gold standard" for a clinician is a double-blind challenge, sometimes referred to as an open label challenge, requiring a period of milk elimination from the infant's diet, however, such challenges are typically refused by around a third or more parents especially in circumstances where reimbursement is not dependent on a positive cow's milk challenge such as in the UK.

The treatments and management for CMA are markedly different than those for colic. The treatment and management of CMA can include a referral to a specialist allergy clinic for allergy testing and can further include a referral to a paediatric dietitian to monitor growth and nutrition. Treatment of CMA typically requires a trial elimination of all cow's milk from the mother's/infant's diet for 2-4 weeks followed by the reintroduction of cow's milk in the home setting to confirm the diagnosis should there be an improvement in symptoms. In contrast there are no set treatments for colic which have sufficient evidence of efficacy to be widely accepted by the medical community. Management of colic includes soothing the infant, holding the infant upright during feeding to prevent them swallowing air, concerted winding of the infant after feeding and providing gentle motion (rocking a crib or the like) to encourage calmness and sleep.

According there is the need to provide a diagnostic tool to assist in the initial distinction of an infant suffering CMA relative to an infant suffering from colic.

SUMMARY OF INVENTION

According to a first aspect of the present invention there is provided therefor a system for use in recognising an infant suffering from cow's milk allergy comprising measuring body movement of the infant, wherein the system comprises computer processing means configured, in use, to:

- receive a video including a sequence of images of an infant moving;
- detect the infant in the video images;
- locate at least one reference point on the infant;
- measure a vector of movement for the or each reference point over a sequence of said images;
- compare the or each vector of movement against a directory of corresponding vectors of movement and determine a proximity value;
- generate a communication in which the proximity value is used to provide an indication of whether the infant is suffering from cow's milk allergy.

According to a second aspect of the present invention there is provided therefor a method for recognising cow's milk allergy in an infant comprising measuring body movement of the infant, wherein the method is performed on a computing device including at least one processor and a memory storing processor-executable codes which, when implemented by the at least one processor, performs the steps of:

- receiving a video including a sequence of images of an infant moving;
- detecting the infant in the video images;
- locating at least one reference point on the infant;

measuring a vector of movement for the or each reference point over a sequence of said images;

compare the or each vector of movement against a directory of corresponding vectors of movement and determine a proximity value;

generating a communication in which the or each proximity value is used to provide an indication of whether the infant is suffering from cow's milk allergy.

According to a third aspect of the present invention there is provided therefor a computer-implemented method for use in recognising an infant suffering from cow's milk allergy comprising measuring body movement of the infant, wherein the method comprises:

receiving a video including a sequence of images of an infant moving;

detecting the infant in the video images;

locating at least one reference point on the infant;

measuring a vector of movement for the or each reference point over a sequence of said images;

compare the or each vector of movement against a directory of corresponding vectors of movement and determine a proximity value;

generating a communication in which the or each proximity value is used to provide an indication of whether the infant is suffering from cow's milk allergy.

According to a fourth aspect of the present invention there is provided therefor a non-transitory processor-readable medium having instructions stored thereon, which when executed by one or more processors, cause the one or more processors to implement a method, comprising:

receiving a video including a sequence of images of an infant moving;

detecting the infant in the video images;

locating at least one reference point on the infant;

measuring a vector of movement for the or each reference point over a sequence of said images;

compare the or each vector of movement against a directory of corresponding vectors of movement and determine a proximity value;

generating a communication in which the or each proximity value is used to provide an indication of whether the infant is suffering from cow's milk allergy.

According to a fifth aspect of the present invention there is provided therefor a system for use in distinguishing between an infant suffering from cow's milk allergy and an infant suffering colic comprising measuring body movement of the infant, wherein the system comprises computer processing means configured, in use, to:

receive a video including a sequence of images of an infant moving;

detect the infant in the video images;

locate at least one reference point on the infant;

measure a vector of movement for the or each reference point over a sequence of said images;

compare the or each vector of movement against a directory of corresponding vectors of movement and determine a proximity value;

generate a communication in which the or each proximity value is used to provide an indication of whether the infant is suffering from cow's milk allergy or colic.

According to a sixth aspect of the present invention there is provided therefor a method for distinguishing cow's milk allergy in an infant and an infant suffering colic comprising measuring body movement of the infant, wherein the method is performed on a computing device including at least one processor and a memory storing processor-executable codes which, when implemented by the at least one processor, performs the steps of:

receiving a video including a sequence of images of an infant moving;

detecting the infant in the video images;

locating at least one reference point on the infant;

measuring a vector of movement for the or each reference point over a sequence of said images;

compare the or each vector of movement against a directory of corresponding vectors of movement and determine a proximity value;

generating a communication in which the or each proximity value is used to provide an indication of whether the infant is suffering from cow's milk allergy or colic.

According to a seventh aspect of the present invention there is provided therefor a computer-implemented method for use in distinguishing between an infant suffering from cow's milk allergy and an infant suffering colic comprising measuring body movement, wherein the method comprises:

receiving a video including a sequence of images of an infant moving;

detecting the infant in the video images;

locating at least one reference point on the infant;

measuring a vector of movement for the or each reference point over a sequence of said images;

compare the or each vector of movement against a directory of corresponding vectors of movement and determine a proximity value;

generating a communication in which the or each proximity value is used to provide an indication of whether the infant is suffering from cow's milk allergy.

According to an eighth aspect of the present invention there is provided therefor a non-transitory processor-readable medium having instructions stored thereon, which when executed by one or more processors, cause the one or more processors to implement a method, comprising:

receiving a video including a sequence of images of an infant moving;

detecting the infant in the video images;

locating at least one reference point on the infant;

measuring a vector of movement for the or each directory point over a sequence of said images;

compare the or each vector of movement against a directory of corresponding vectors of movement and determine a proximity value;

generating a communication in which the or each proximity value is used to provide an indication of whether the infant is suffering from cow's milk allergy or colic.

Neither CMA or colic are recognised as a movement disorder disease or movement disorder condition. Furthermore, the medical profession is not taught nor encouraged to distinguish between colic and CMA based on the movement of the infant. Nevertheless, the inventor of the present invention has identified that infants suffering with CMA have vectors of movement that are distinct from infants not suffering with CMA and/or from infants suffering with colic. Based on this surprising and inventive realisation the inventor was able to create systems and methods to recognise an infant suffering from CMA and/or distinguish between an infant suffering from CMA and an infant suffering from colic.

Preferably any feature of the infant that can be identified and the movement of said feature calculated can be a reference point. The most preferred reference points for the present invention being one or more the infant's: head (including but not limited to one or both eye centres, nose tip); torso (including but not limited to chest at mid-point between shoulders, either or both shoulders, stomach at mid-point between chest and groin); arms including but not limited to shoulder, elbow, wrist, hand); legs (including but not limited to hip, knee tip; ankle, big toe tip); back (including but not limited to mid-point between shoulders); etc.

Additionally or alternatively, two or more reference points can be linked by a straight line to create a reference line. Preferably three reference points can be linked by a straight line to create the reference line. For example, the three reference points of the infant's shoulders and the mid-point therebetween could be linked with a straight line to create the reference line. Preferably intersecting reference lines may be created, for example, three reference points of the infant's shoulders and the mid-point therebetween could be one reference line, and an intersecting reference line could be created by linking the reference points of the infant's nose tip with the stomach at mid-point between chest and groin and groin.

Preferably any feature of the infant capable of displaying a gesture wherein said feature can be identified and the creation of the gesture be detected or the absence of said gesture be detected can be a reference point. The most preferred reference points for gesture detection for the present invention being: detecting first forming of the hands; arching of the infant's back; curling of toes; a kicking motion of the legs; one or more pre-characterised facial gestures; etc.

The video comprises a sequence of frames with each frame corresponding to an image still. The video has a frame rate that corresponds to the numbers of frames over a period of time, for example frames per second.

The video may be of any suitable duration in which at least some movement of the infant can be observed, preferably only the infant appears in the video. Preferably however, the video of the infant is at least 10 seconds in duration. Even more preferably the video of the infant is at least 20 seconds in duration. Most preferably the video of the infant is at least 30 seconds in duration.

At least a portion of the video may contain images of the infant presenting symptoms of discomfort. Preferably at least 25% the video contains images of the infant presenting symptoms of discomfort. Even more preferably at least 50% the video contains images of the infant presenting symptoms of discomfort. Most preferably at least 75% the video contains images of the infant presenting symptoms of discomfort.

More than one video of the infant may be presented to the method and system of the present invention. Preferably at least three videos of the infant are presented to the method and system of the present invention. Where more than one video of an infant is presented to the method and system of the present invention one of said videos may be of the infant presenting symptoms of discomfort and one of said videos may be of the infant presenting not symptoms of discomfort.

The video preferably shows a majority of the infant, wherein the majority is defined as an infant has volume and the video captures greater than 50% of the infant's volume within the images thereof. The more of an infant that is captured within the video the more reference points can be detected to better determine one or more vectors of movement. More preferably the video captures greater than 75% of the infant's volume within the images. Most preferably the video captures substantially the entirety of the infant within the images.

The vector of movement is preferably calculated from recognising the speed and distance of movement of the or each reference point and/or reference line(s). Most preferably a vector of movement is calculated for a single reference point. A high value of a vector of movement for a particular reference point and/or reference line(s) would be indicative of a severe movement of the infant, whereas a low value of a vector of movement would be indicative of a normal movement of the infant.

In an example, the vector of movement has a direction component that corresponds to the direction that the reference point and/or reference line(s) is moved. The direction may be with respect to a reference direction or directions, for example the reference direction(s) may correspond to a set of features on the baby. The speed may be determined based on how the reference point and/or reference line is moved in each frame and the frame rate of the video.

Directory vectors of movement are a collection of vectors of movement that may be attained by determining respective vectors of movement in infants (suffering from CMA (diagnosed), in infants suffering from colic (suspected), and infants not obviously suffering with any ailment as a control. The collection of vectors of movement may be compared to create an average value for a particular vector of movement for an infant suffering from CMA (diagnosed) or suffering from colic or not suffering from any ailment. Alternatively or additionally, the collection of vectors of movement may be compared to create a range of values for a particular vector of movement for an infant suffering from CMA (diagnosed) or an infant suffering from colic or an ailment-free infant.

Proximity value is preferably calculated from the amount of deviation of at least one vector of movement from the or each corresponding directory vector of movement. In other words, if the system or method of the present invention was used to determine a vector of movement of an infant's head, the corresponding directory vector(s) of movement would be those directory vectors of movement for the corresponding infant body part/reference point which in this case would be those infants' heads.

Preferably the proximity value is calculated from more than one vector of movement and their deviation from their corresponding directory of respective vectors of movement. Even more preferably the proximity value is calculated from more than five vectors of movement and their deviation from their corresponding directory of respective vectors of movement. Most preferably the proximity value is calculated from more than five vectors of movement and their deviation from their corresponding directory of respective vectors of movement. It is preferable for the proximity value to be calculated from more than one vector of movement measured on the infant since the greater the volume the greater the accuracy of the proximity value.

Where more than one vector of movement and their deviation from their respective corresponding directory vector of movement is used to calculate the proximity value, then preferably a series of intermediate proximity values are produced from each deviation which are averaged to produce the proximity value.

Alternatively, where more than one vector of movement and their deviation from their respective corresponding directory vector of movement is used to calculate the proximity value, then preferably a series of intermediate proximity values are produced from each deviation from which the median is taken to produce the proximity value.

As a further alternative, where more than one vector of movement and their deviation from their respective corresponding directory vector of movement is used to calculate the proximity value, then preferably a series of intermediate proximity values are produced from each deviation from which the mode is taken to produce the proximity value.

Preferably the indication communicated by the systems and/or methods of the present invention will be on a scale with one end of said scale being indicative of a diagnosis of colic alone and the other end of said scale being indicative of a diagnosis of CMA. Where the indication is on a scale, any suitable means can be used for said scale, preferably however the indication is provided by a numerical scale, and even more preferably said numeric scale is numbered 1 to 4 wherein a 1 on the scale would be indicative of a diagnosis of colic alone and where a 4 on said scale would be indicative of a diagnosis of CMA alone.

Where more than one video of the same infant is presented to the system(s) and/or method(s) of the present invention preferably an indication will be produced that is the average or the median or the mode of the respective proximity values for each respective proximity value to create interim indication In a preferred arrangement the systems and methods of the present invention utilize learning machine learning algorithms wherein for infants in which the system and or method produces an indication of whether the infant is suffering from CMA or from colic or not suffering from either CMA or colic and a medical practitioner has made a diagnosis, whether informed by said indication or not, the result of the diagnosis is fed into the directory of vectors to further refine same.

The systems and methods of the present invention may be supplemented by incorporating the infant's physical patient data such as length/height of infant and/or weight.

In an example, the method comprises a step of reorienting the video to a standard direction. The video of the baby may be analysed to determine the orientation and then calibrated to correspond to the orientation of videos used to form the directory of corresponding vectors.

BRIEF DESCRIPTION OF THE DRAWINGS

Embodiments of the invention will now be described, by way of example only, with reference to the following drawings in which.

DEFINITIONS

"Client Device" in the context of the present invention this refers to any computational machine that can connect to and communicate with a communications network to obtain information and/or resources from one or more application server systems. As such a client device may include one or more of the following: a mobile phone; a laptop computer; a desktop computer; a tablet; a smart phone; or any other communication device that a user may use to access a communications network.

"Communications Network" in the context of the present invention refers to any suitable network, networks or portions of one or more networks that define a set of protocols to allow one software application to communicate with another software application without regard to the hardware and or operating systems on which said software applications are operating on. Examples of suitable communications networks may include one or more of the following either alone or in combination: the internet; an intranet; a virtual private network (VPN); a local area network (LAN); a wireless LAN (WLAN); a wide area network (WAN), a wireless WAN (WWAN); a cellular telephone network; or the like.

"Carrier Signal" in the context of the present invention refers to any intangible medium capable of storing, encoding, or carrying instructions for execution by the computational machine communicated by one or more communication networks. Examples of suitable carrier signals include, but are not limited to, digital and/or analog communications signals and/or other intangible medium to facilitate communication of such instructions.

The various systems and methods of the present invention performed in whole or in part on one or more processors that are configured by software to perform the relevant operations "Processing Means" in this context refers to any circuit or virtual circuit that can manipulate data values according to control signals and which are capable of producing a corresponding output signal or signals that may be implemented to operate a computational machine. By way of example a processing means can include or of more of the following: a central processing unit (CPU); a graphics processing unit (GPU); an application specific integrated circuit (ASIC); a radio-frequency integrated circuit (RFIC) or any combination thereof.

DESCRIPTION OF AN EMBODIMENT

Figure 1:
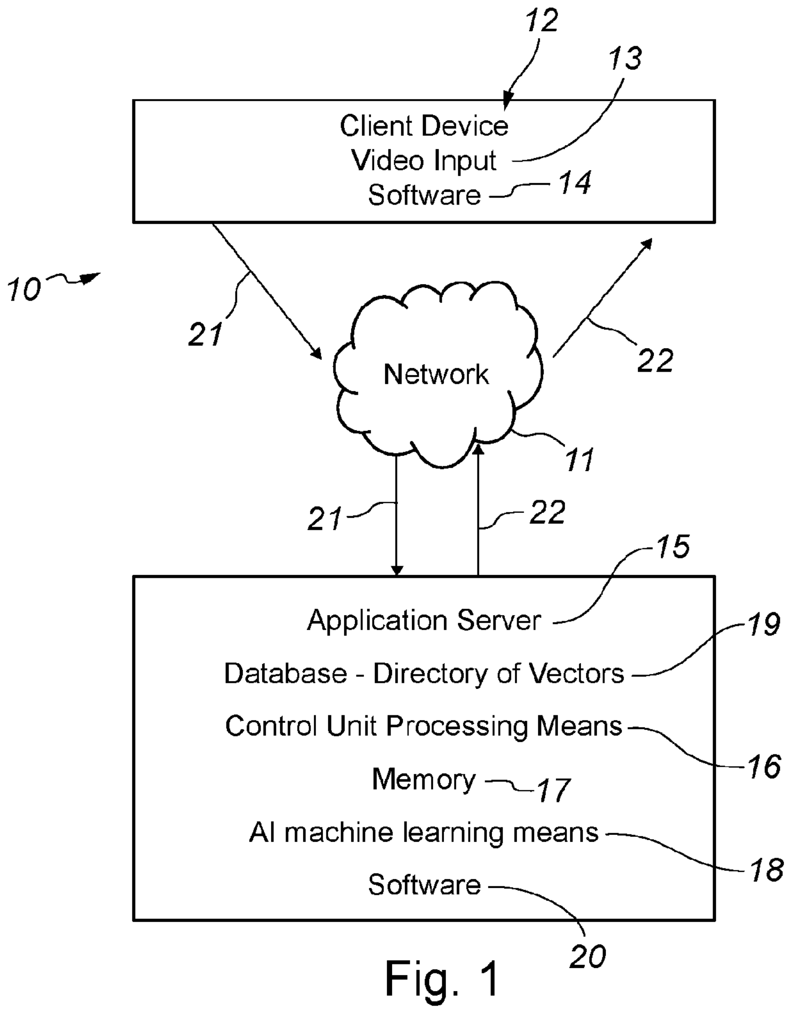
FIG. 1 illustrates a high-level architecture of a system according to the present invention.

Turning to the drawings, FIG. 1 illustrates a high-level architecture 10 of a client device 12 capable of connecting to and communicating through a communications network 11 to communicate with an application server 15. The client device 12 may be any suitable computation machine but here is a laptop containing video input 13 in the form of one or more video files wherein each video file consists of a video including a sequence of images of an infant 30 moving. The client device 12 also contains software 14. The communications network 11 may be any suitable network but here is the internet. Connected to the communication network 11 is an application server 15. The application server 15 comprises control unit processing means 16, memory/storage means 17, machine learning algorithms means 18 (so-called AI artificial learning means 18), a database containing at least a directory of vectors of movement 19 and software 20.

In operation of the methods and/or systems of the present invention a user would identify a video 13 or videos of an infant on the client device 12. Using the software 14 on the client device 12, the user instructs the client device 12 to submit the video 13 to the application server 15. The software 14 on the client device 12 then creates a carrier signal 21 containing at least the video 13 which is sent to the applications server 15 through the communications network 11.

On receipt of the carrier signal 21 the application server 15 uses a combination of the software 20, memory means 17 and database 19, all under the control of the processing means 16 to analyse the carrier signal 21 and the video 13 it contains. The video 13 can contain more than one video of the infant. Ideally the video 13 contains at least one video of the infant presenting symptoms of discomfort. Preferably the video 13 shows a majority of the infant, wherein the majority is defined as an infant has volume and the video captures greater than 50% of the infant's volume within the images thereof since the more of an infant that is captured within the video 13 the more reference points can be detected to better determine one or more vectors of movement. Preferably the or each video of the infant is at least 10 seconds in duration, but more preferably at least 20 seconds in duration and, most preferably, at least 30 seconds in duration.

Figure 2:
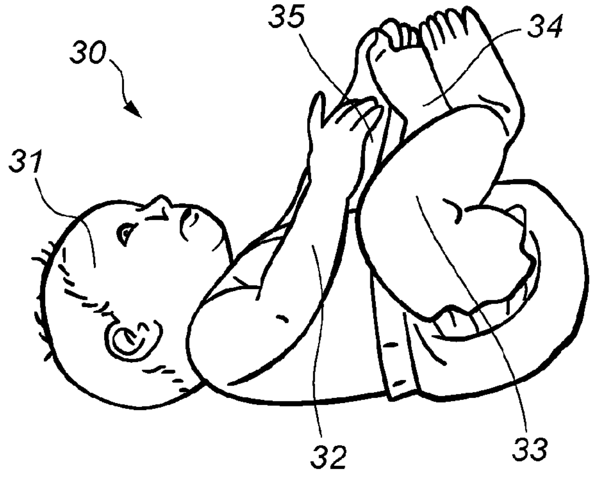
FIG. 2 illustrates an infant captured in a video.

The software 20 analyses the video 13 to identify one or more reference points on the infant 30. Any feature of the infant 30 that can be identified and the movement of said feature calculated can be a reference point. Referring to FIG. 2 an infant 30 is illustrated in which several reference points have been identified, namely the head 31, the right arm 32, the right leg 33, the left leg 34 and the left arm 35. The vector of movement of each reference point 31-35 is measured throughout the video against time to determine the speed and distance of movement of each reference point.

The resultant vector(s) of movement for each reference point of the infant 30 in the video 13 can then be compared against the directory of corresponding vectors of movement in the database 19. The directory of corresponding vectors of movement are a collection of vectors of movement that may be attained by determining respective vectors of movement in infants (suffering from CMA (diagnosed), in infants suffering from colic (suspected), and infants not obviously suffering with any ailment as a control and then stored in the database 19. The collection of vectors of movement may be compared to create an average value for a particular vector of movement for an infant suffering from CMA (diagnosed) or suffering from colic or not suffering from any ailment. Alternatively or additionally, the collection of vectors of movement may be compared to create a range of values for a particular vector of movement for an infant suffering from CMA (diagnosed) or an infant suffering from colic or an ailment-free infant.

Figure 3:
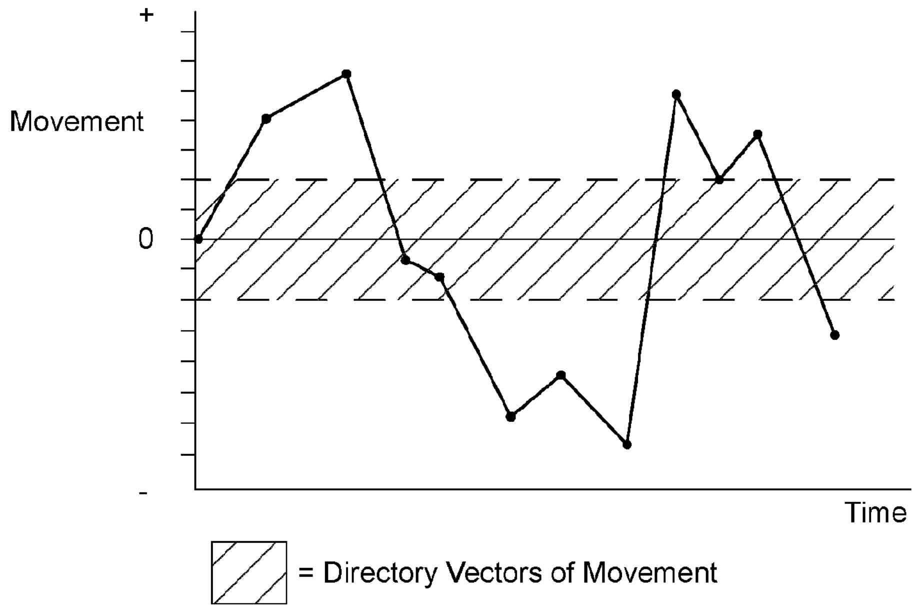
FIG. 3 illustrates an example graph of a movement of a reference point of an infant in a video.
Figure 4:
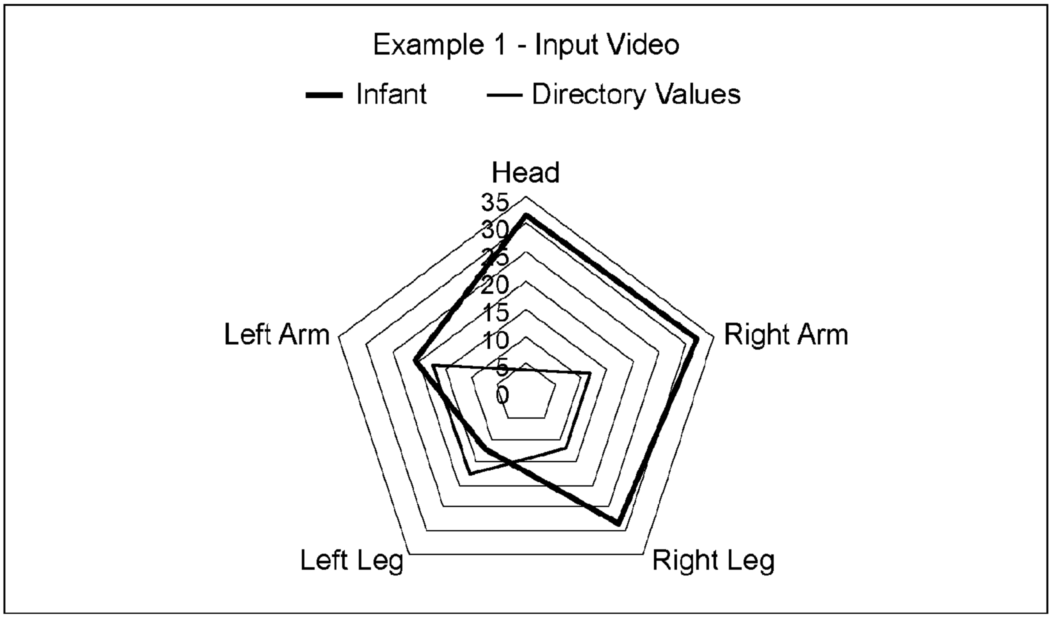
FIG. 4 illustrates an example graph of average movement of several reference points of an infant in a video.

Referring to FIGS. 3 and 4, examples of the how the methods and systems of the present invention track one or more reference points of an infant 30 to determine a vector of movement. In FIG. 3 the reference point 32 on the right arm of the infant 30 is tracked to create a graph of movement of the reference point against time. On the graph there is also shown the average range of directory of vectors of movement for the right arm of infants suffering with colic.

FIG. 4 shows a radar graph of averaged vectors for the five reference points 31-35 of the infant 30 overlaid on the directory of corresponding vectors of movement of infants suffering from colic.

One or more of the components of the application server will analyse the comparison between the vector of movement of each reference point and the directory of corresponding vectors of movement to determine a proximity value. The proximity value is preferably calculated from the amount of deviation of the or each vector of movement from the or each directory of corresponding vectors of movement. Where more than one vector of movement and their deviation from their respective directory of corresponding vectors of movement is used to calculate the proximity value, then preferably a series of intermediate proximity values are produced from each deviation which are averaged or the like to produce the proximity value.

The processing means 16 can use the proximity value to calculate an indication, said indication being indicative of a diagnosis of the extent to which the infant 30 is suffering with CMA or colic. Preferably the indication is on a scale with one end of said scale being indicative of a diagnosis of colic alone and the other end of said scale being indicative of a diagnosis of CMA. The application server is configured to create a carrier signal 22 to carry the indication through the communications network 11 to the client device 12. On receipt of the carrier signal 22, the client device 12 is configured to display the indication to the user. For example, if the indication is on a numerical scale, the indication would be in the form of a number where one end of the numerical scale would be indicative of a diagnosis of colic alone and a number at the other end of the scale would be indicative of a diagnosis of CMA.

Preferably the application server 15 also uses the machine learning algorithms means 18 to review the vector of movement data used to provide the indication and determine whether the data therefrom can be used to bolster the data in the database 19 to further improve, refine or optimise future reviews of videos of infants suspected of suffering from either CMA or colic.

In the foregoing example the application server 15 identifies the reference points in the video 13 of the infant. In an alternative or additional embodiment, the identification of the reference points on the infant takes place on the client device 12 rather than on the application server 15. In this embodiment of the operation of the methods and/or systems of the present invention a user would identify a video 13 or videos of an infant on the client device 12. Using the software 14 on the client device 12, the user instructs the client device 12 to submit the video 13 to the application server 15. The software 14 analyses the video 13 to identify one or more reference points on the infant 30 captured in the video and the software measures the vector of movement of the or each reference point. The software 14 on the client device 12 then creates a carrier signal 21 containing at least the vector(s) of movement which is sent to the applications server 15 through the communications network 11.

On receipt of the carrier signal 21 the application server 15 uses a combination of the software 20, memory means 17 and database 19, all under the control of the processing means 16 to analyse the carrier signal 21 and the vectors of movement(s) it contains. The vector(s) of movement of the infant can then be compared against the directory of corresponding vectors of movement in the database 19 as discussed for the earlier embodiment.

Additionally or alternatively after the software 20 has identified a series of reference points on the infant, the software 20 is configured to link two or more reference points together with a straight reference line. The linking of three reference points with a straight line to create the reference line is generally preferred. The software 20 analyses the video 13 to identify one or more reference lines on the infant 30. The vector of movement of each reference line is measured throughout the video against time to determine the speed and distance of movement of each reference line. The resultant vector(s) of movement for each reference line of the infant 30 in the video 13 can then be compared against the directory of corresponding vectors of movement in the database 19.

Two intersecting reference lines may be identified and the vector of movement of the intersecting reference lines is measured throughout the video against time to determine the speed and distance of movement of said intersecting reference lines. The resultant vector(s) of movement for the intersecting reference lines of the infant 30 in the video 13 can then be compared against the directory of corresponding vectors of movement in the database 19.

One or more of the components of the application server will analyse the comparison between the vector of movement of each reference line and the directory of corresponding vectors of movement to determine the proximity value.

For intersecting reference lines, one or more of the components of the application server will analyse the comparison between the vector of movement of those intersecting reference lines and the directory of corresponding vectors of movement to determine the proximity value. Alternatively, for intersecting reference lines, one or more of the components of the application server will analyse the comparison between the vector of movement of each reference lines and the resultant proximity values would be intermediate proximity values which are averaged or the like to produce the proximity value.

Where a proximity value is determined from one or more reference points and from one or more reference lines, the resultant proximity values would be intermediate proximity values which are averaged or the like to produce the proximity value.

The processing means 16 can use the proximity value to calculate an indication, said indication being indicative of a diagnosis of the extent to which the infant 30 is suffering with CMA or colic. Preferably the indication is on a scale with one end of said scale being indicative of a diagnosis of colic alone and the other end of said scale being indicative of a diagnosis of CMA. The application server is configured to create a carrier signal 22 to carry the indication through the communications network 11 to the client device 12. On receipt of the carrier signal 22, the client device 12 is configured to display the indication to the user. For example, if the indication is on a numerical scale, the indication would be in the form of a number where one end of the numerical scale would be indicative of a diagnosis of colic alone and a number at the other end of the scale would be indicative of a diagnosis of CMA.

Preferably the application server 15 also uses the machine learning algorithms means 18 to review the vector of movement data used to provide the indication and determine whether the data therefrom can be used to bolster the data in the database 19 to further improve, refine or optimise future reviews of videos of infants suspected of suffering from either CMA or colic.

The description of the systems and methods of the present invention including the instructions, sequences, and computation machine specifications are illustrative and that alternative instructions, sequences, and computation machine specifications could be used without deviating from the innovation at the core of said systems and methods of the present invention. Indeed, one suitable alternative system architecture that could be used for the systems and methods of the present invention is described in US2009/110736 and the features of said system are incorporated herein by reference. Another suitable system that can be deployed to facilitate the systems and methods of present invention is described in US2015/286858 and the features of said system are incorporated herein by reference.

All of the features disclosed in this specification (including any accompanying claims, abstract and drawings), and/or all of the steps of any method or process so disclosed, may be combined in any combination, except combinations where at least some of such features and/or steps are mutually exclusive.

Each feature disclosed in this specification (including any accompanying claims, abstract and drawings) may be replaced by alternative features serving the same, equivalent or similar purpose, unless expressly stated otherwise. Thus, unless expressly stated otherwise, each feature disclosed is one example only of a generic series of equivalent or similar features.

The invention is not restricted to the details of the foregoing embodiment(s). The invention extends to any novel one, or any novel combination, of the features disclosed in this specification (including any accompanying claims, abstract and drawings), or to any novel one, or any novel combination, of the steps of any method or process so disclosed.

The invention claimed is:

1. A system for use in recognizing an infant suffering from cow's milk allergy comprising measuring body movement of the infant, wherein the system comprises computer processing means configured to:

receive a video including a sequence of images of an infant moving;

detect the infant in the video images;

locate at least one reference point on the infant in the video images, wherein the at least one reference point is a body part of the infant;

measure at least one vector of movement for the at least one reference point over a sequence of said images;

compare the at least one vector of movement for the at least one reference point against at least one directory of corresponding vectors of movement and determine at least one proximity value, wherein the at least one directory of corresponding vectors of movement comprises a collection of vectors of movement attained by determining respective vectors of movement in infants suffering from cow's milk allergy and in infants not obviously suffering with any ailment as a control, and wherein the at least one proximity value is calculated from the amount of deviation of the at least one vector of movement from the at least one directory of corresponding vectors of movement;

generate a communication in which the at least one proximity value is used to provide an indication of whether the infant is suffering from cow's milk allergy; and display the communication of the indication of whether the infant is suffering from cow's milk allergy to a user.

2. The system according to claim 1, wherein the reference point is one or more of the infant's: head; torso; arms; elbows; hands; legs; knees; feet; and back.

3. The system according to claim 1, wherein two or more reference points are linked by a straight line to create at least one reference line.

4. The system according to claim 1, wherein the video of the infant is at least 10 seconds in duration.

5. The system according to claim 1, wherein more than one video of the infant is used by the system.

6. The system according to claim 1, wherein the vector of movement is calculated from recognizing the speed and distance of movement of the at least one reference point.

7. The system according to claim 3, wherein the vector of movement for the at least one reference point is calculated from recognizing the speed and distance of movement of the at least one reference line.

8. The system according to claim 1, wherein the at least one proximity value is calculated from more than one vector of movement for more than one reference point and their deviation from more than one corresponding directories of respective vectors of movement.

9. A method for recognizing cow's milk allergy in an infant comprising measuring body movement of the infant, wherein the method is performed on a computing device including at least one processor and a memory storing processor-executable codes which, when implemented by the at least one processor, performs the steps of:

receiving a video including a sequence of images of an infant moving;

detecting the infant in the video images;

locating at least one reference point on the infant in the video images, wherein the at least one reference point is a body part of the infant;

measuring at least one vector of movement for the at least one reference point over a sequence of said images;

comparing the at least one vector of movement for the at least one reference point against at least one directory of corresponding vectors of movement and determining at least one proximity value, wherein the at least one directory of corresponding vectors of movement comprises a collection of vectors of movement attained by determining respective vectors of movement in infants suffering from cow's milk allergy and in infants not obviously suffering with any ailment as a control, and wherein the at least one proximity value is calculated from the amount of deviation of the at least one vector of movement from the at least one directory of corresponding vectors of movement;

generating a communication in which the at least one proximity value is used to provide an indication of whether the infant is suffering from cow's milk allergy; and display the communication of the indication of whether the infant is suffering from cow's milk allergy to a user.

10. The method according to claim 9, wherein the reference point is one or more of the infant's: head; torso; arms; elbows; hands; legs; knees; feet; and/or back.

11. The method according to claim 9, wherein two or more reference points are linked by a straight line to create at least one reference line.

12. The method according to claim 9, wherein the video of the infant is at least 10 seconds in duration.

13. The method according to claim 9, wherein more than one video of the infant is used by the system.

14. The method according to claim 9, wherein the at least one vector of movement for the at least one reference point is calculated from recognizing the speed and distance of movement of the at least one reference point.

* * * * *